United States Patent [19]
Racz et al.

[11] Patent Number: 6,146,380
[45] Date of Patent: Nov. 14, 2000

[54] BENT TIP ELECTRICAL SURGICAL PROBE

[75] Inventors: Gabor B. Racz, Lubbock, Tex.; Philip Finch, Parkerville, Australia

[73] Assignee: Radionics, Inc., Burlington, Mass.

[21] Appl. No.: 09/004,992

[22] Filed: Jan. 9, 1998

[51] Int. Cl.[7] .................................................. A61B 18/14
[52] U.S. Cl. .............................. 606/41; 607/99; 607/105; 607/113; 607/116
[58] Field of Search .................................... 607/116, 117, 607/99, 98, 105, 113; 606/41, 48–50

[56] References Cited

U.S. PATENT DOCUMENTS

| | | | |
|---|---|---|---|
| 3,828,780 | 8/1974 | Morrison, Jr. | 606/49 |
| 3,943,932 | 3/1976 | Woo | 607/116 |
| 4,301,802 | 11/1981 | Poler | 606/48 |
| 4,411,266 | 10/1983 | Cosman | 606/49 |
| 5,433,739 | 7/1995 | Sluijter et al. | 607/99 |
| 5,605,539 | 2/1995 | Buelna et al. | 606/49 |
| 5,807,395 | 9/1998 | Mulier et al. | 606/41 |

FOREIGN PATENT DOCUMENTS 1391626  4/1988  U.S.S.R. .................. 606/41

*Primary Examiner*—Lee Cohen

[57] ABSTRACT

A medical needle or cannula for stimulation or ablation includes a rigid bent tip for simplified placement at target sites within a patient's anatomy. The curved tip or shaft is used to steer the device within the patient's body and to avoid critical anatomical structures. The device is partially insulated and has a tip that is at least partially electrically exposed; a connection to an external signal generator provides electrical stimulation or high-frequency heating of the patient's tissue proximal to the exposed tip. The device includes a longitudinal passage to facilitate the injection of fluids or the insertion of instruments through the cannula or needle.

12 Claims, 2 Drawing Sheets

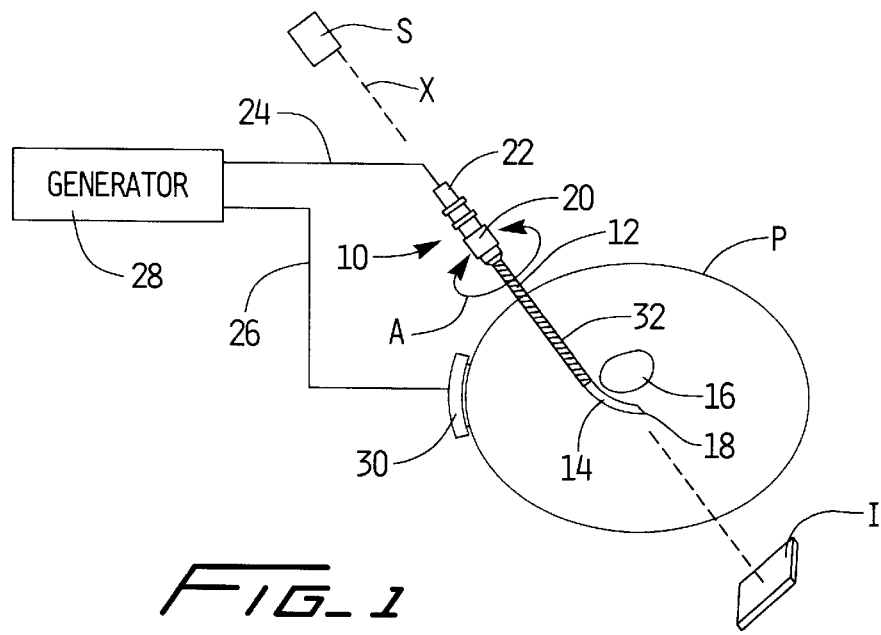
FIG_1
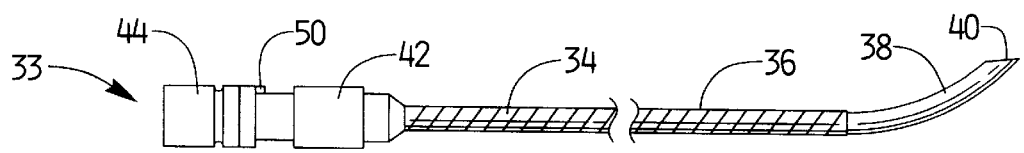
FIG_2A
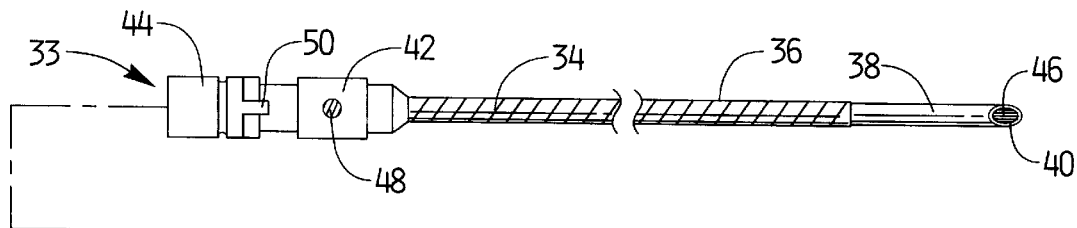
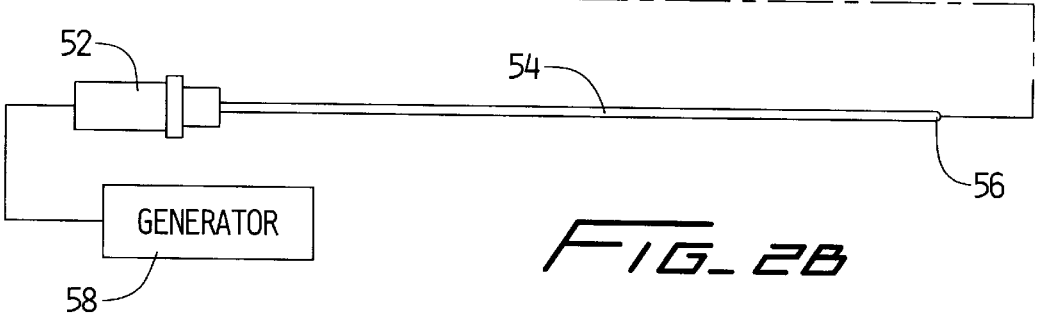
FIG_2B

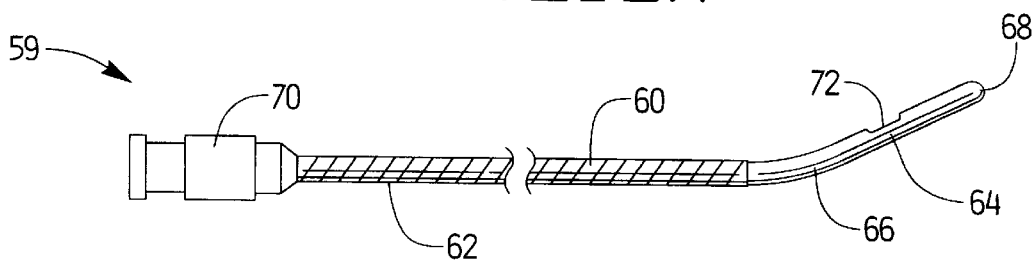
FIG_3A
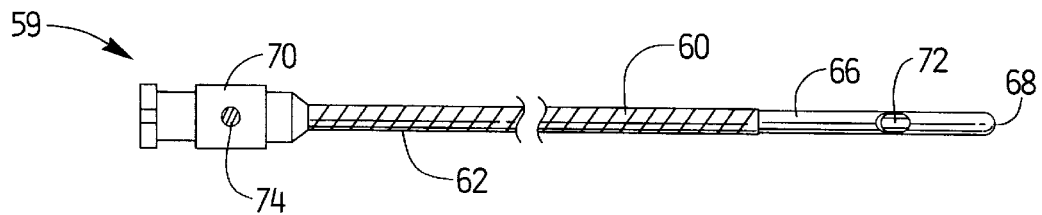
FIG_3B

BENT TIP ELECTRICAL SURGICAL PROBE

FIELD OF THE INVENTION

The invention relates to a system for pain relief employing electrical stimulation or high frequency delivery techniques, and more particularly to an apparatus for pain relief that delivers electrical stimulation pulses or high-frequency signals to the vicinity of a neural structure via an electrical needle or cannula.

BACKGROUND OF THE INVENTION

It has been found that relief from localized pain can be achieved in many patients through the delivery of electrical stimulation or high-frequency signals to a target region. To accomplish this, stimulation or radio-frequency electrodes are placed within a patient's body. Those electrodes are connected to a generator of stimulation electrical signals or high-frequency electrical signals to deliver energy to tissue and neural structures. This can result in anesthesia, temporary relief, or long-term relief from pain. Examples of electrodes, signal generators, and methods usable for this purpose can be found in the product line of Radionics, Inc., of Burlington, Massachusetts.

A wide variety of electrode geometries can be used in such applications. For example, an electrode unit having an insulated shaft and an exposed electrical tip, which can be pointed, blunt and rounded, or open, are suitable for various procedures. Pointed tips are self-penetrating, while rounded tips can be used in soft tissue such as the brain. Open tips can be used to deliver a liquid or other diagnostic or therapeutic agent, or a stylet or an endoscopic tool, to the target while simultaneously performing electrical treatment. Radio-frequency electrodes are commonly used; these typically have an insulated straight tubular metal shaft with an electrically exposed tip. Connection at the hub or proximal end of the electrode is made to an external signal generator capable of generating stimulation or high-frequency energy. In the course of treatment, the electrode is inserted into the patient's tissue, and signals from the signal generator are thereby delivered into the region of the patient's tissue surrounding the tip of the electrode.

The SMK Needle electrodes from Radionics are in some ways representative of electrodes typically used in pain relief procedures. The SMK Needles have plastic hubs and metal shafts that are insulated over most of their length. An exposed tip is a straight extension of the metal tubing shaft of the needle. An obdurating stylet is inserted into the needle during insertion into the patient's tissue. Once it has been inserted, the stylet is withdrawn and the radio-frequency or stimulation probe is inserted. The probe is connected to an external signal generator. Contrast agents or anesthetic fluids can be injected into the tissue near the tip through the hollow needle.

A common use for the Radionics SMK Needle is in the stimulation and denervation of a patient's spine. In this procedure, the SMK Needle electrodes are inserted, while viewed via X-ray or fluoroscope, near the facet joints or other neural structures of the spine. Anesthetic or diagnostic localization agents can be injected through the needles, and stimulation testing can then be performed. Radio-frequency heat ablation of a portion of the patient's tissue near the tip of a needle is routinely performed. Hence, proper placement of the needle tip in the complicated structure of a patient's spine requires great skill by the treating clinician. One limitation of the straight electrodes typically used in such procedures is that the needles may need to be withdrawn and re-inserted multiple times to achieve the proper target region for the needle tip.

The need to access other complex structures, such as lumbar-sacral discs, particularly where there is a high pelvic brim in males and in those individuals having extreme degenerative narrowing, makes needle placement even more difficult. The nerve root in the lower spine may be accidentally impaled; this presents a serious medical risk to the patient. Again, the use of straight, self-penetrating needles is limited somewhat in that the tip is collinear with the needle shaft, so navigating the tip to avoid critical structures requires redirection of the shaft and repeated manipulation. It would be desirable to facilitate such redirection in ways unachievable by a straight needle, reducing the need to withdraw and reinsert the needles.

Moreover, the straight, exposed tip of a straight needle cannot hug the contour of a curved bony structure such as the superior articular facet, which proximates target nerves. This can present a restriction to target location in some situations.

It is desirable to be able to redirect or steer the tip of the electrode, which for straight needles can be tedious and difficult. It is further desirable to be able to control the tip of a needle by mere shaft rotation or other means of manipulation.

Stimulation and high frequency electrodes having expandable and flexible curved tips are known. Examples of such electrodes are the TEW Electrode Kit and the ZHK Electrode Kit, both manufactured by Radionics. Those electrodes both have flexible, curved tips, which extend from the straight shaft of an enclosing cannula to extend off-axis in an arc. This is useful in certain neural regions such as the trigeminal ganglion or the pituitary gland, or any area where the target region is very soft or fluid filled. Such flexible off-axis electrodes have a limitation that there tips cannot penetrate tough tissue or encounter hard bone without being damaged or diverted.

It is observed that neither straight needles nor flexible electrodes have the desired characteristics for use in difficult-to-reach target regions. Accordingly, it would be desirable to have an electrode cannula for stimulation or ablation that avoids the limitations of the art.

SUMMARY OF THE INVENTION

The present invention is directed to a system and method for delivering anesthesia, pain relief, or other treatment involving a firmly curved tip needle electrode. In one example, a needle comprising a metal tubular shaft having insulation over a portion of the shaft further includes an exposed and bent tip portion. This bend can be fabricated into the metal shaft so that it is relatively permanent and robust. The bent needle can then be connected to a signal generator to supply stimulation, high frequency, or pulsed high frequency signals for the purpose of stimulation, heat ablation, or other anesthetic electrical action.

Such a robust bent tip would make possible the re-direction of the position and orientation of the tip near neural structures, bone, or critical structures, without the need to fully withdraw and re-insert the needle. Alteration of the direction of the needle hub presents another advantage. It can be advantageous with a bent tip to follow neural structures, hug bony structures, and avoid certain organs or regions at risk, which can be useful in certain clinical applications.

A further advantage of a permanently bent or curved needle is that its position can be altered to some degree by merely rotating the needle shaft; this is not the case with straight needles. Accordingly, some position adjustments can be performed with fewer manipulations than a straight needle would require. Moreover, a bent or curved needle having a pointed tip mounted at the distal end of a relatively rigid tubular or solid shaft enables self-penetration of tough tissue near hard, bony structures. This kind of manipulation is not generally possible with side outlet-bearing electrodes such as Radionics' TEW and ZHK kits because of the fragility and flexibility of their tips.

The advancement and manipulation of a bent needle or cannula can be performed under X-ray or other guidance by the clinician to place the bent tip in its target position. This provides an added advantage over a straight needle or cannula.

These features and advantages as well as others will be apparent in the detailed description that follows.

BRIEF DESCRIPTION OF THE DRAWINGS

In the drawings, which constitute a part of this specification, embodiments are exhibited in various forms, and are set forth specifically:

FIG. 1 is a schematic diagram of a bent tip electrical needle connected to an electrical signal generator, in accordance with the present invention;

FIG. 2 includes FIG. 2A and FIG. 2B, which show schematic side elevation and orthogonal view representations of a bent tip needle with a stylet, an electrical probe, and a signal generator; and FIG. 3 includes FIG. 3A and FIG. 3B, which show a side elevation view and an orthogonal view, schematically rendered, of a blunt bent-tipped needle with index markings and an injection port.

DETAILED DESCRIPTION OF THE INVENTION

Referring initially to FIG. 1, a radio-frequency electrode cannula 10 having a shaft 12 is shown inserted into a portion P of a patient's body. The shaft 12 of the electrode cannula 10 has a rigid, permanent, off-axis bend at a distal tip 14. The cannula 10 can be inserted directly through the skin of the body portion P to locate the tip 14 in a target position within the body. For illustrative purposes, an internal anatomical structure 16 is shown, and the curved tip 14 is directed around the anatomical structure 16. This can be accomplished by manipulation of the shaft 12 upon insertion, making use of an off-axis, rigid, curved, self-penetrating point 18 defined by the tip 14. The shaft 12 can be axially rotated, as illustrated in FIG. 1 by an arrow A. The tip 14 will accordingly alter its azimuthal orientation within the body portion P with respect to the fixed position of the shaft 12. Therefore, for a given direction of insertion, the curvature of the tip 14 permits a variety of tip positions to be reached. In this way, by a process of inserting the electrode cannula 10 longitudinally and rotating it azimuthally according to the arrow A, the tip 14 can be steered or directed in accordance with the operating clinician's needs and actions.

The electrode cannula 10 further comprises a hub 20. The hub 20 is capable of accommodating an electrical probe 22, which includes a segment that is inserted into and received by the shaft 12 of the cannula 10. This physical relationship between the probe 22 and the shaft 12 facilitates electrical contact between the two elements.

An electrical signal is transmitted to a target region within the body portion P by way of a pair of electrical connections 24 and 26. A first electrical connection 24 couples the cannula 10 to an external signal generator 28 by way of the hub 20 and the probe 22. A second electrical connection 26 connects the external signal generator 28 to a reference electrode 30 in contact with the patient's body portion P. As discussed above, the signal generator 28 can be a source of electrical stimulation, pulsed high-frequency stimulation signals, high frequency signals, pulsed radio-frequency output, or other electrical waveforms. The two electrical connections 24 and 26, in cooperation with the cannula 10 and the reference electrode 30, form a complete electrical circuit permitting current flow. For background information on how this has been accomplished in past systems, see E. R. Cosman and B. J. Cosman, "Methods of Making Nervous System Lesions," in R. H. Wilkins and S. S. Rengachary, eds., *Neurosurgery*, New York: McGraw-Hill (1984), v. III, pp. 2490–98.

Generally, by the connections set forth above, an output of the signal generator 28 is conveyed via the first electrical connection 24 to the probe 22, the cannula 10, and its tip 14. This causes electrical stimulation or high-frequency heating of tissue near the exposed electrical tip 14. This practice is well known in the arts of stimulation and ablation.

However, in accordance with an embodiment of the invention, as shown in the illustration of FIG. 1, the tip 14 of the cannula 10 has a bent configuration, and the straight portion 32 of the shaft 12 is at least in part electrically insulated, as indicated by the hatched area of FIG. 1. The cannula 10 is inserted into the patient's body portion P under X-ray guidance. One common practice is to locate an X-ray source S along a desired axis for needle placement. An image detector I disposed on an opposite side of the body portion P then receives those X-rays transmitted along an axis X of the cannula 10, thereby permitting verification of the proper location and orientation of the tip 14 of the cannula 10. When bony anatomy corresponds to the appropriate direction of insertion by the clinician, the cannula 10 can be inserted into the patient's body portion P along that direction. See E. R. Cosman and B. J. Cosman, "Methods of Making Nervous System Lesions," in R. H. Wilkins and S. S. Rengachary, eds., *Neurosurgery*, New York: McGraw-Hill (1984), v. III, pp. 2490–98. This is known as the "needle view" method of needle placement.

Commonly, a C-arm fluoroscopic X-ray machine includes the source S and the image detector I. When the cannula 10 has been moved into a longitudinal position near the target, the angular orientation of the tip 14 can be manipulated into one of many possible rotation angles, as indicated by the arrow A. As an illustration, the curved tip 14 can be steered around the anatomical structure 16. The surface of the exposed tip 14 can be positioned to "hug" or otherwise approach the contour of the anatomical structure 16. The structure 16 may be a bony structure that has nerves running near its surface, and the clinician may desire to modify or coagulate those nerves by electrical signals sent from the tip 14 by the signal generator 28. This procedure can be more effective when performed with the rigid bent tip 14 of the invention than with a traditional straight or flexible tip.

FIG. 2 shows another embodiment of the present invention. By way of a further explanation of a specific embodiment, FIG. 2 illustrates various additional features of a curved or bent-tipped electrical needle. In an illustrative embodiment, the shaft 34 comprises a hollow metal tube with an insulated portion 36 illustrated by hatched lines, as shown in FIG. 1. The distal curved tip portion 38 is an extension of the metal tube; it defines a permanent or semi-permanent curve that has an at least partially uninsulated surface portion. In the embodiment illustrated in FIG. 2, the bend is approximately curvilinear and defined by a radial arc. The tip portion 38 of the shaft 34 has a distal pointed end 40, which as described above can be useful in penetrating tough tissue. A hub 42 can be metal, or alternatively plastic when radiotranslucency is desired.

The embodiment set forth in FIG. 2A is shown with a stylet inserted. Though most of the stylet is not visible, because it is obscured by the shaft 34, the hub 44 of the stylet is visible at the proximal end of the device. Traditional needle sets that include insulated metal shafts with matching stylets are common in medical practice. See, for example, the SMK needles and cannulae made by Radionics.

FIG. 2B is another view of the needle illustrated in FIG. 2A, but additional features are visible. The pointed end 40 defines an opening 46 that is capable, as discussed above, of dispensing diagnostic or therapeutic liquids, or of allowing a stylet or endoscopic instrument to pass. Also shown is an index dot 48 on the hub which indicates the orientation of the bent tip 38. In a preferred embodiment, the index dot 48 is located at the same radial position on the shaft 34 as the bent tip 38 and pointed end 40. An index notch 50, which indexes the stylet and its hub 44 with respect to the shaft 34 and the orientation of the tip 14, is further provided. Index notches such as notch 50 are commonly used in needle and stylet sets. An electrical probe 52 is receivable by the shaft 34 when the stylet is removed; it has a probe shaft 54 and a probe tip 56. In one embodiment of the invention, the probe tip 56 comprises a temperature sensor. See, for example, the SMK needles and cannulae made by Radionics.

The apparatus illustrated in FIGS. 2A and 2B is used as follows. The cannula 33, with a stylet positioned in the shaft 34, is inserted into the patient's body portion P (FIG. 1) either percutaneously or intraoperatively. An X-ray viewer (comprising a source S and an image detector I, as disclosed above) can verify the position and orientation of the bent tip 38 in relation to desired anatomical targets. The stylet is then removed, and the probe 52 is inserted into the shaft 34. The probe 52 is connected to the signal generator 58, and the process of electrical stimulation, high-frequency heating, or other electrical application can be made. Electrical signals from the signal generator 58 are communicated to the exposed distal tip 38 by way of contact between the probe shaft 54 and an internal lumen defined by the electrode shaft 34. If the electrode shaft 34 or cannula is a metal tube and the probe shaft 54 has a metal outer surface, then this can be accomplished simply through physical contact between the probe shaft 54 and the electrode shaft 34. When the application of therapeutic electrical signals is complete, the probe 52 is withdrawn from the cannula 33, and the electrode can then be withdrawn from the patient.

FIG. 3 illustrates a further embodiment of the invention, useful in certain other applications. FIGS. 3A and 3B represent alternative views of the same embodiment, and as such, reference numerals are shared between the figures. In the cannula 59 illustrated in FIG. 3A, a shaft 60 has an insulated proximal portion 62 (dashed-line portion) and an uninsulated distal tip section 64. The shaft 60 defines a permanent, rigid bend portion 66. The bent portion 66 can be in the insulated proximal portion 62 or in the distal tip section 64 depending on the application; in the illustrated embodiment, the bent portion 66 is part of the distal tip section 64. The tip section 64 also has a relatively straight portion. The tip section 64 terminates in a blunt or rounded end 68, which in this embodiment is closed (in contrast to the open ends 18 and 40 of FIGS. 1 and 2). A hub 70 is a standard hypodermic needle or luer type hub, capable of connection to stylets, electrical probes, syringes, or injection tubes. For example, precision nerve blocks by injection of local anesthetic can be used to confirm the exact position of a target in a diagnostic procedure. This may then be a precursor to other options such as stimulation, radio-frequency heating, pulsed radio-frequency heating, and other procedures discussed herein.

A portal window 72 is shown in the tip portion 64 of the bent needle or cannula 59 of FIG. 3. In this way, anesthetic, contrast fluids, or other diagnostic or therapeutic agents injected through the hub 70 will be discharged through the window 72 on a lateral portion of the tip 64. Again, an index marker 74 indicates to the clinician the direction of the bent tip 64, even when the tip 64 is not directly visible. The index marker 74 is preferably placed on a proximal portion of the cannula 59 or other instrument, and in the illustrated embodiment on the hub 70. The index marker 74 facilitates steering the bent tip during placement of the cannula in the patient's tissue; it also indicates the direction of the window 72 if fluids are to be injected interstitially.

In one embodiment of the invention, as illustrated in FIG. 3, the window 72 lies on an inside portion of the curved or bent tip 64. In this way, the directionality of the injected anesthetic or contrast fluid can be maintained toward the inside of the needle's curve.

Cannulae such as those shown in FIGS. 1–3, particularly the sharp-tipped embodiments illustrated in FIGS. 1 and 2, must be placed with accuracy and care to avoid injury to critical neural structures. The use of a C-arm X-ray machine, such as that schematically indicated by the source S and image detector I of FIG. 1 is a common imaging method used for insertion and placement. The "needle view" or "beam view" approach used with such an imaging method is in common practice. However, it should be noted that alternate imaging methods for needle or cannula placement can employ CT, MRI, ultrasound, or other techniques.

The advantages and uses of the bent tip electrical cannulae disclosed and claimed herein are apparent in light of the foregoing structural details. Bent tip electrical probes according to the invention provide improved target positioning and safer placement in comparison to traditional treatment modalities. For example, directional steering is facilitated by the curve in the distal end of a spinal needle formed in accordance with the embodiments of FIGS. 1 and 2. Directional changes during needle insertion can be achieved more easily and less traumatically than would otherwise be possible with a straight-tipped electrode, reducing the need for repeated painful withdrawals and re-insertions.

With a bent-tipped electrode or cannula, rotating the hub while the device is inserted can facilitate steering along a desired insertion path. In this way, a curved or bent-tipped device is steered down the X-ray beam, or perpendicular to the plane of the "needle view," toward the target. The exact skin entry point used to reach a particular target is less important with a bent-tipped device, because a considerable degree of directional control is possible during manipulation of the needle toward the target.

A further advantage of using a small-gauge spinal needle with a curved or bent distal end is that it can be accurately steered into narrow and relatively difficult-to-access portions of a patient's spine. For example, access to the lumbar sacral disc is often difficult with straight needles, especially with the high pelvic brim in males and the extreme degenerative narrowing seen in the bony structures of some patients. In these situations, the use of a straight-tipped needle can increase the risk of L5 nerve root puncture or injury. With the present invention and a curved-tipped spinal needle, this danger can be avoided and the risks thereby minimized. The bent tip enables a curved approach to the spinal structures and the intravertebral disc. It facilitates the placement of the curved tip in such a way as to hug or conform the outer aspect of the superior articular facet. Moreover, the curved needle of the present invention can be steered around corners, underneath bone grafts, and past spinal fixation devices such as metal plates that may have been implanted on the spine in previous surgical procedures.

Yet another advantage of the system and method of the present invention is that certain other anatomical structures are easier to access with a curved-tipped needle. The lumbar joint, which is a complex curved structure, and the sacroiliac joint, which is partially obscured to a posterior approach by the ilium, are clinical examples in which this advantage is particularly important. Moreover, a fine degree of directional control can be achieved in the context of nerve blocking of spinal roots in these areas and in the nerve root canals. As in all surgical procedures, avoidance of injury to delicate anatomic structures is of primary importance. As discussed above, this can be accomplished by making small adjustments to the direction of the curved needle tip, by altering the azimuthal orientation of the shaft during placement.

Directional control is particularly advantageous in cervical discography, which involves access via an oblique tract that avoids structures such as the esophagus, which is laden with bacteria. The curved tip of a needle according to the invention, placed in this case near the anterior aspect of the intervertebral joint, is then steered by its curvature into the disc. It is even possible to alter the position of the needle in the disc once it has entered the disc itself.

Another important clinical application is lateral entry to the tarricopalatine fossa via the tarricomaxillary fissure, which is partially obstructed by the convex posterior wall of the maxilla. A needle with a terminal or distal curve can be used with advantage to negotiate this difficult entry tract. As with entry to the spinal nerve root canal, small changes in the orientation of the curved distal tip are possible with the present invention, without the need to withdraw and insert the needle multiple times.

Furthermore, the uninsulated portion of the tip 14, 38, or 64 (FIGS. 1–3) can be made to lie parallel to neural structures which are on a curvilinear geometry. This configuration is advantageous in those clinical situations in which a radio-frequency heat lesion is to be made on the neural structures, as the uninsulated tip used to generate the lesions conforms better to the target neural structures.

The apparatus of the present invention enables access to multiple tip positions and orientations with fewer needle insertions than with conventional straight-tipped needles. This is achieved by rotating the hub of the cannula 59 (FIG. 3, for example) to cause the curved tip 64 to access different target volumes. For example, when treating the medial branches of the posterioramus in the cervical region, straight electrodes generally must be placed at several points, since each facet joint is enervated by more than one division of the posterioramus nerve. The curved needle of the present invention reduces the need for multiple placements. Furthermore, one can achieve varied directionality within bony openings such as the foramen ovale for access to the trigeminal ganglion or the spinal foramena for access to spinal root ganglia.

As illustrated in FIGS. 2 and 3, the curved needles of the invention may have color-coded markers such as the index dot 48 (FIG. 2) and the index marker 74 (FIG. 3). These markers indicate the orientation of the curved tip for convenient steering or navigating of the cannula 33 or 59 once it has been placed within the patient's tissue. Color coding at the proximal end of the cannula may be used to indicate the degree of curvature of the tip; it is expected that different curvatures will most advantageously be used in different patients and applications, where the target regions have varied geometries.

Those individuals skilled in the art will recognize that many variations of the electrode geometries depicted in FIGS. 1–3 are possible without departing from the invention. Various sized electrodes can be made, from extremely small gauges (e.g., 30 gauge) to much larger sizes (e.g., 10 gauge). Also, the shape and degree of tip curvature may vary widely. The shape of the tip and the extent of insulation vs. exposed electrode can be variable, depending on the application. For example, in FIGS. 1 and 2, the exposure of the tip 14 or 38 may be only on one side of the cannula to facilitate directional stimulation or ablation; the exposed portion of the tip need not extend all the way around the tip azimuthally.

Moreover, as discussed above, the tip of an electrode constructed according to the invention may have a sharp or a blunt point. A blunt or rounded end can be preferable in some situations, as it will deflect away from a neural structure or blood vessel rather than pierce or injure it. As an example, in stimulation and lessening applications, a needle tip may need to be placed at the lumbar sympathetic nerve chain, which passes close to the ventral nerves and the lumbar plexies. In this situation, a blunt-tipped needle is safer. Another advantage of a blunt-tipped needle is that it can give a greater degree of "feel" as it passes through various tissue structures and planes. For example, there is a distinct "popping" sensation as a blunt tip passes through the psoas fascia on its way to the sympathetic nerve chain. To insert a blunt-tipped needle, a traditional pointed intravenous cannula can be passed or punctured through the skin to a certain level, with the blunt-tipped needle according to the invention then inserted into the same tract, or even through the cannula. Deeper tissues tend to present less resistance to a blunt-tipped needle than the skin and shallow structures, unless there is substantial scarring, and therefore a blunt-tipped needle can frequently be manipulated very easily.

In some situations, a sharp needle (such as those illustrated in FIGS. 1 and 2) may be easier to insert or manipulated. For example, in a conscious patient, a pointed needle is inserted more comfortably, whereas for a sedated patient a blunt-tipped needle may be used. In another context, the medial branch of the superior ramus is better approached with a sharp-tipped needle or cannula because major neural structures do not lie in the desired pathway to the lumbar transfer process or the waste of the articulate pillar in the cervical spine. In the pointed-tipped needle shown in FIG. 2, the aperture or opening 46 for injecting fluids lies at the very distal end of the tip 38, in contrast to the inside wall used for the window 72 of FIG. 3.

Various forms and embodiments of the bent tip needle or cannula are provided herein involving various shapes, sizes, forms, and configurations of the cannula and associated stylet, electrical connection, temperature monitoring scheme, signal generator, and other components. However, it should be recognized that other forms of the present invention may become apparent to those skilled in the art. For example, as discussed above, various configurations of tip geometry, bluntness or sharpness, degree of curvature, position of fluid injection ports, and the insulation configuration may be devised. Moreover, the curvature of the tip may be permanently established upon manufacture of the device, or in an alternative embodiment, may be modified by bending a semi-malleable structure at the time of surgery by the clinician. A family of needles or cannulae with different geometries may be created according to the invention.

It should be noted that the terms needle, probe, cannula, etc. as used herein all denote medical and surgical tools that can accommodate the bent tip structure disclosed and claimed. There is no intention to restrict any particular embodiment of the invention to fewer than all of the foregoing implements. Furthermore, certain exemplary clinical applications have been discussed herein as those in which the invention can be successfully employed to the clinician's advantage. However, the invention is not limited to use in such applications, and other medical and surgical procedures would be apparent to a practitioner of ordinary skill.

Thus, while certain exemplary structures and operations have been described, the invention is not so limited, and its scope is to be determined according to the claims set forth below.

What is claimed is:

1. A hollow cannula for insertion into a patient's body and adapted to receive an electrical signal from a signal generator to be transmitted to a target region in the patient's body, comprising:

an electrically insulated elongated shaft defining a longitudinal passage;

a distal tip portion coupled to the elongated shaft, the distal tip portion defining an aperture in communication with the longitudinal passage, the aperture adapted to allow introduction of fluid into the patient's body; and an electrical connection for receiving the electrical signal, the electrical connection coupled to the distal tip portion;

wherein the distal tip portion includes an uninsulated, rigidly bent portion to facilitate placement of the distal tip portion at the target region, and wherein at least a portion of the distal tip portion comprises an electrically conductive surface that defines a treatment area.

2. The cannula of claim 1, further comprising a hub mounted at a proximal end of the shaft remote from the distal tip portion, wherein the hub includes a marker to indicate the orientation of the bent portion when the cannula is inserted into the patient's body.

3. The cannula of claim 1, wherein the distal tip portion defines a sharp end to facilitate insertion into the patient's body.

4. The cannula of claim 1, wherein the distal tip portion defines a blunt end.

5. The cannula of claim 4, wherein the blunt end is closed to fluid flow.

6. The cannula of claim 5, wherein the longitudinal passage is adapted to pass a fluid flow, and wherein the distal tip portion defines a radial window adapted to allow fluid passage for delivery to the patient's body.

7. The cannula of claim 1, wherein the electrical connection comprises a probe adapted to be received by the shaft.

8. The cannula of claim 1, wherein the elongated shaft comprises a metal tube.

9. The cannula of claim 1 where the rigidly bent portion is curvilinear.

10. The cannula of claim 1 where the rigidly bent portion is defined by a radial arc.

11. A hollow cannula for insertion into a patient's body and adapted to receive an electrical signal from a signal generator to be transmitted to a target region in the patient's body, comprising:

an electrically insulated elongated shaft defining a longitudinal passage;

a distal tip portion coupled to the elongated shaft, the distal tip portion defining an aperture in communication with the longitudinal passage, the aperture adapted to allow introduction of fluid into the patient's body; and means for receiving the electrical signal, the means coupled to the distal tip portion;

wherein the distal tip portion includes an uninsulated, rigidly bent portion to facilitate placement of the distal tip portion at the target region, and wherein at least a portion of the distal tip portion comprises an electrically conductive surface that defines a treatment area.

12. An instrument for transmitting an electrical signal to a target region in a patient's body, comprising:

an electrically insulated elongated shaft;

a distal tip portion coupled to the elongated shaft, the distal tip portion defining an aperture, the aperture adapted to allow introduction of fluid into the patient's body, wherein the distal tip portion includes an uninsulated, rigidly bent portion to facilitate placement of the distal tip portion at the target region, and wherein at least a portion of the distal tip portion comprises an electrically conductive surface that defines a treatment area; and an electrical connection for receiving the electrical signal, the electrical connection coupled to the distal tip portion.

* * * * *